US008252228B1

(12) United States Patent
Freeman et al.

(10) Patent No.: US 8,252,228 B1
(45) Date of Patent: Aug. 28, 2012

(54) METHODS FOR STERILIZING CARRIERS FOR TREATMENT OF A KIDNEY

(75) Inventors: Abigail Freeman, Del Mar, CA (US); Thierry Glauser, Redwood City, CA (US); Paul M. Consigny, San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/250,488

(22) Filed: Oct. 13, 2008

(51) Int. Cl.
*A61L 2/00* (2006.01)

(52) U.S. Cl. .............. 422/1; 422/205; 128/898; 604/82; 604/83; 604/84; 604/85; 604/86; 604/87; 604/88; 604/89; 604/90; 604/91; 604/92

(58) Field of Classification Search .................. 128/898; 422/205, 26; 604/82–92
See application file for complete search history.

(56) References Cited

U.S. PATENT DOCUMENTS

| | | | | |
|---|---|---|---|---|
| 4,141,887 A * | 2/1979 | Seufert | ........................ | 530/383 |
| 4,507,283 A * | 3/1985 | Smith | ........................ | 424/94.64 |
| 4,595,560 A * | 6/1986 | Buchner et al. | ................. | 422/26 |
| 4,769,974 A * | 9/1988 | Davis | ............................. | 53/433 |
| 4,774,091 A * | 9/1988 | Yamahira et al. | ............. | 424/426 |
| 4,966,899 A * | 10/1990 | Kohno et al. | ................. | 514/197 |
| 5,192,743 A * | 3/1993 | Hsu et al. | .......................... | 514/8 |
| 5,242,989 A * | 9/1993 | Bening et al. | ................. | 525/384 |
| 5,291,991 A * | 3/1994 | Meyer | ........................... | 206/221 |
| 5,595,760 A * | 1/1997 | Cherif-Cheikh | .............. | 424/464 |
| 5,650,172 A * | 7/1997 | Matsuda et al. | .............. | 424/489 |
| 6,207,178 B1 * | 3/2001 | Westesen et al. | ............. | 424/405 |
| 6,519,919 B1 * | 2/2003 | Takenouchi et al. | ........... | 53/431 |
| 6,608,061 B2 * | 8/2003 | Yonetani et al. | .............. | 514/241 |
| 6,693,093 B2 * | 2/2004 | Chowdhary et al. | .......... | 514/185 |
| 6,749,844 B2 * | 6/2004 | Riffle et al. | ................. | 424/78.08 |
| 6,896,845 B2 * | 5/2005 | Kaieda | ........................... | 419/18 |
| 7,214,799 B2 * | 5/2007 | Khalifah et al. | .............. | 546/300 |
| 7,556,826 B2 * | 7/2009 | Sung et al. | ..................... | 424/456 |
| 7,612,181 B2 * | 11/2009 | Wu et al. | ..................... | 530/387.3 |
| 2003/0099674 A1 * | 5/2003 | Chen | ............................. | 424/400 |
| 2004/0010224 A1 * | 1/2004 | Bodmeier | ....................... | 604/82 |
| 2004/0082602 A1 * | 4/2004 | Hagen et al. | .................. | 514/291 |
| 2004/0091546 A1 * | 5/2004 | Johnson et al. | ............... | 424/501 |
| 2004/0192658 A1 * | 9/2004 | Hunter et al. | ................. | 514/152 |
| 2005/0003007 A1 | 1/2005 | Boix et al. | | |
| 2005/0186261 A1 * | 8/2005 | Avelar et al. | .................. | 424/445 |
| 2007/0071764 A1 * | 3/2007 | Sullivan et al. | ............. | 424/178.1 |

FOREIGN PATENT DOCUMENTS

WO    WO2006002365    *   1/2006

* cited by examiner

*Primary Examiner* — Nicholas Lucchesi
*Assistant Examiner* — Scott Medway
(74) *Attorney, Agent, or Firm* — Randy Shen; Blakely Sokoloff Taylor & Zafman LLP (57) ABSTRACT

A kit is described including at least one container including a predetermined quantity of sterilized biodegradable carriers in a powder form having a treatment agent disposed therein. The kit further includes a delivery device for delivering the predetermined quantity of sterilized biodegradable carriers with the treatment agent disposed therein to a treatment site. In other embodiments, methods are described for producing the sterilized treatment agent loaded biodegradable carriers and delivering the sterilized carriers to a treatment site.

13 Claims, 5 Drawing Sheets

METHODS FOR STERILIZING CARRIERS FOR TREATMENT OF A KIDNEY

FIELD

Techniques for fabrication of sterilized carriers for delivery to a kidney for inhibiting nephropathy or end-stage renal disease.

BACKGROUND

Nephropathy is a disease that typically develops over a prolonged period (e.g., 10-15 years) during which time the ability of the kidneys to properly function diminishes. Once the disease has progressed to end-stage renal disease (ESRD), a kidney transplant or dialysis is the only treatment option. The disease is caused, for example, by immune disorders (e.g. IgA nephropathy) or diabetes (e.g. diabetic nephropathy). In either case, nephropathy is characterized by the trapping of protein deposits, such as, the protein immunoglobulin A (IgA), inside glomerular capillaries of the kidney. These glomerular capillaries serve as the kidney's filtration system to filter waste and water from the blood. The protein deposits prevent the glomerular capillaries from properly filtering the blood resulting in high protein levels in the urine.

Once the glomerular capillaries are damaged, they cannot be repaired. Thus, treatment of nephropathy typically involves slowing the progression of the disease rather than curing it. Treatment consists of, for example, administration of therapeutics, such as angiotensin converting enzyme (ACE) inhibitors which reduce urine protein levels. A solution of the therapeutic can be delivered to the kidneys systemically or locally.

Prior to delivery of the therapeutic to the desired tissue, the therapeutic must be sterilized. There are many techniques for carrying out sterilization including chemical treatment, heat treatment, filtration, irradiation, or other methods. Since sterilization methods have the potential to affect properties of the therapeutic solution, factors such as the type of therapeutic, properties of the therapeutic solution and the particular use of the therapeutic in the organism must be considered when selecting the sterilization method.

In addition to the type of therapeutic and its use, a desired sterility level must be considered when selecting a sterilization method. The required sterility assurance level (SAL) for a product is dependent on the intended use of the product. SAL refers to the probability of a viable microorganism being present on a product unit after sterilization. For medical devices in particular, the level of sterility for a Class I device as per United States Food and Drug administration (FDA) classifications, which presents minimal risk of harm to the user and are simpler than Class II and Class III devices, will be different than the level required for Class III devices which are characterized by the FDA as devices that support or sustain human live, are of substantial importance in preventing impairment of human health, or which present a potential, unreasonable risk of illness or injury.

SUMMARY

According to an embodiment, kits and methods for sterilizing quantities of treatment agent loaded carriers for delivery to a kidney are described. Representatively, in one embodiment, a kit includes at least one container including a predetermined quantity of a powder of sterilized biodegradable carriers having a treatment agent encapsulated therein. The container may be a syringe or vial. The treatment agent includes a property to inhibit a biological process contributing to nephropathy. Such biological processes include, but are not limited to, changes in glomerular basement membrane, changes in mesangial matrix deposition and podocyte apoptosis. The kit further includes a delivery device for delivering the predetermined quantity of sterilized biodegradable carriers with the treatment agent disposed therein to a treatment site. The delivery device can include, for example, a catheter assembly.

In another embodiment, a method is described. The method includes introducing a predetermined quantity of biodegradable carriers having a treatment agent disposed therein into a container. The predetermined quantity of biodegradable carriers includes an amount of the treatment agent sufficient for treating the desired tissue region. The container with the treatment agent loaded carrier therein is lyophilized to form a powder of the predetermined quantity of biodegradable carriers in the container. The container and the biodegradable carriers in the container are then sterilized. Suitable sterilization techniques include chemical techniques such as an ethylene oxide gas technique, Noxilizer™ technique and gas plasma techniques as well radiation techniques using, for example, electron beams and gamma rays.

In still further embodiments, a method includes re-suspending a sterilized powder comprising a predetermined quantity of treatment agent loaded carriers within a container to form a solution. The method further includes introducing a delivery device to a point within a renal system. As previously discussed, the delivery device can include, for example, a catheter assembly. The method further includes delivering the solution comprising a predetermined quantity of sterilized biodegradable carriers through the delivery device to a treatment site within the renal system from the container. The treatment site can include a renal vessel and/or glomerular capillaries within the kidney.

Some embodiments include sterilizing a predetermined amount of a treatment agent and sterilizing a carrier solution separate from the treatment agent. The sterilized treatment agent and sterilized carrier solution are combined to form sterilized carriers comprising the treatment agent therein. The sterilized carriers comprising the treatment agent therein are packaged and moisture is removed from the packaged sterilized carriers.

BRIEF DESCRIPTION OF THE DRAWINGS

The features, aspects, and advantages of the invention will become more thoroughly apparent from the following detailed description, appended claims, and accompanying drawings.

DETAILED DESCRIPTION

The embodiments disclosed herein produce accurate quantities of sterile carriers (e.g. microparticles or nanoparticles)

having a treatment agent disposed therein within a container that can be used to deliver the treatment agent to tissues within the renal system. The sterilization techniques disclosed herein allow for sterilization of the carriers and associated components (e.g. containers) without substantially modifying the morphology or properties of the carriers or treatment agent therein. Although the techniques are described as being used with the kidney and its related tissues, it is contemplated that the techniques can further be used to produce sterile treatment agent carriers for use in connection with tissues associated with other organs of the body, such as the heart.

Sterilization may be achieved using an aseptic processing technique or a terminal sterilization technique. Aseptic technique refers to a process in which individual product components are sterilized separately and the final package assembled in a sterile environment. Terminal sterilization refers to the process of sterilizing the final packaged product.

Typically, small amounts of the treatment agent need to be incorporated into the carriers. The techniques disclosed herein allow predetermined amounts of treatment agent to be incorporated into carriers, for example, microparticles (e.g. microspheres) or nanoparticles (e.g. nanospheres), and stored within containers for later use. In some embodiments, the treatment agent loaded carriers are then sterilized within the container to ensure that the carriers are free from contaminants prior to delivery to a desired tissue region. In other embodiments, each of the components (e.g. treatment agent, carriers and containers) are sterilized separately and then combined. The sterilization techniques produce sterilized units having the same characteristics.

Terminal Sterilization

Figure 1:
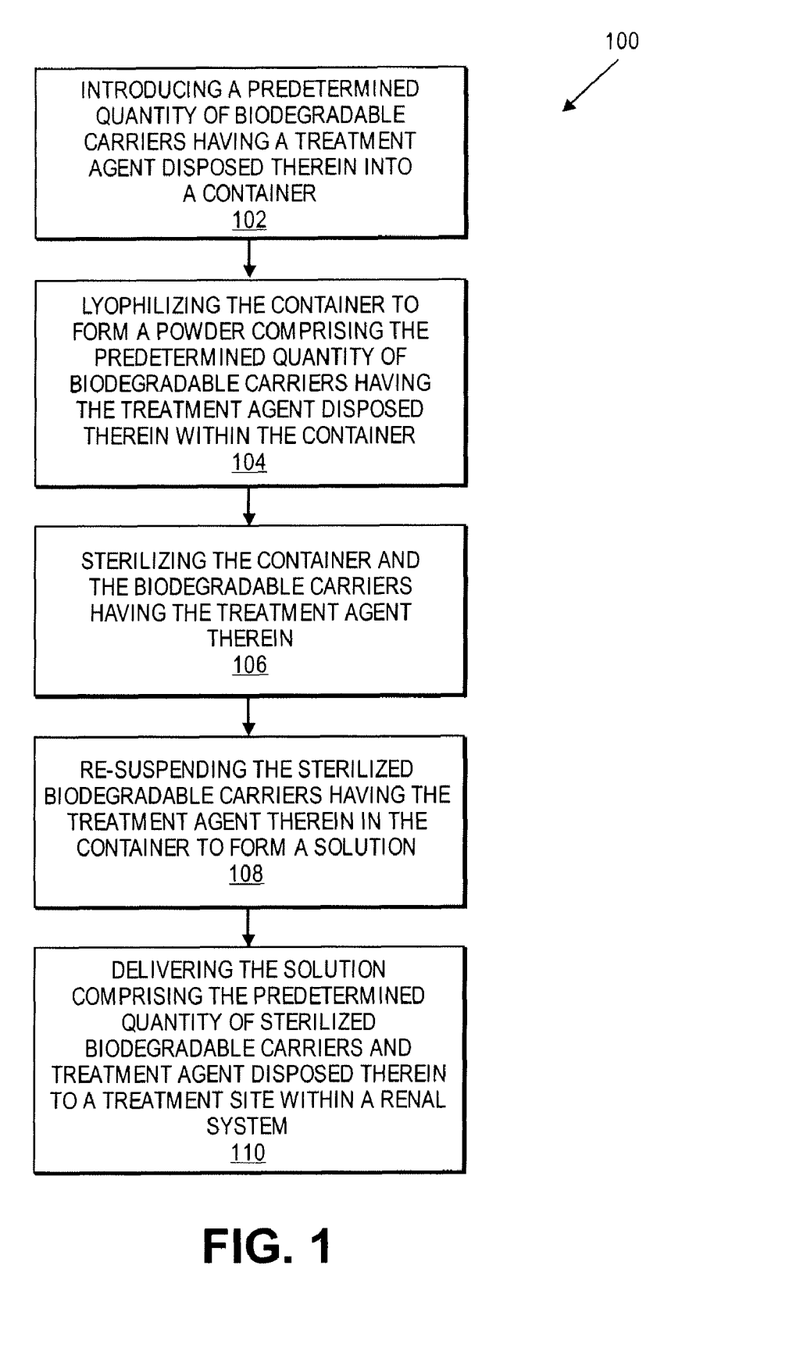
FIG. 1 illustrates a flow chart of a method for preparing and delivering a sterilized treatment agent to a kidney.

FIG. 1 shows a flow chart of a method for preparing and delivering a sterilized treatment agent to a kidney. In one embodiment, the method includes a terminal sterilization technique. The method includes introducing a predetermined quantity of biodegradable carriers having a treatment agent disposed therein into a container (block 102). The predetermined quantity can be any amount of carriers having an effective amount of the treatment agent for treatment of the desired tissue. In this aspect, the quantity of carriers and amount of treatment agent therein may vary depending upon the treatment agent used and tissue to be treated. Representatively, where the treatment agent is an mTOR inhibitor such as everolimus or zotarolimus and the tissue to be treated is that of the glomerulus, the predetermined quantity of carriers having an effective amount of the treatment agent disposed therein may be about 1 to 10 carriers per glomerulus or about 1 to 10 million per kidney.

The biodegradable carrier is a carrier made of any material capable of incorporating a treatment agent and being decomposed within the body to release the treatment agent. Representatively, the carrier is made of a polymer material such as poly(lactic-co-glycolic acid) (PLGA). In some embodiments, the carrier is a nanoparticle (e.g., nanosphere) or microparticle (e.g., microsphere). The treatment agent is incorporated within the carriers using the techniques described more fully below. The amount of treatment agent incorporated into the carriers may be a small amount. For example, from about 5% to about 50% by weight of a solution in the carrier. In some embodiments, the amount is from 1% to 55% or from 10% to 45%.

In one embodiment, the quantity of treatment agent loaded carriers is determined by dispersing a desired amount of the treatment agent loaded carriers in an aqueous medium to form a solution having a known amount of the treatment agent. Representatively, the aqueous medium is sterile filtered saline. It is important that the carriers be evenly dispersed throughout the aqueous medium. In this aspect, the carriers are coated with a material that allows the carriers to go into solution quickly and not adhere to one another. Representatively, in embodiments where the carrier is made of a PLGA material, the coating is a polylactic acid (PLA). In still further embodiments, other techniques such as vortexing can be used to ensure the carriers are evenly dispersed in solution.

Alternatively, the quantity of treatment agent loaded carriers placed in the container is determined by weighing the carriers.

In some embodiments, the container holds a volume of from five milliliters (mL) to 20 mL of solution. In still further embodiments, the container holds from 10 mL to 15 mL of solution. The container can be a syringe or a vial. The container is made of any material compatible with the carriers and treatment agents disposed therein. The material must also be able to withstand the sterilization processes described herein. Representatively, the container is made of a glass or a polymer material.

Prior to sterilization, moisture is removed from the container. In some embodiments, the container having the carriers therein is lyophilized to produce a powder of carriers within the container (block 104). The term "powder" as used herein refers to a dry substance composed of a number of finely dispersed particles. In some embodiments, the container with the solution therein is processed using a conventional lyophilizer such as that available from Labconco Corporation of Kansas City, Mo. In embodiments where the container is a syringe, the plunger of the syringe is removed so that the syringe can fit onto a conventional lyophilizer shelf. The specific lyophilization parameters (e.g. length of time, temperature, pressure, etc.) used to remove the moisture may vary depending upon the amount of aqueous medium in the container. For example, the sample can be maintained for 48 hours under a reduced pressure of less than $10^{-5}$ Mpa with a cooling element at about −50 to −75 degrees C. Once the moisture is removed, a known quantity of the treatment agent loaded carriers is left in each container in a powder form.

In some embodiments where the container is a syringe, prior to sterilization, a filter is placed on the luer tip of the syringe to facilitate sterilization of a re-suspending liquid drawn into the container after sterilization. Representatively, the filter is a 0.2 micrometer filter.

In some embodiments, the container loaded with the carriers is sealed within pouch 502 (see FIG. 5) prior to sterilization. Pouch 502 is a porous pouch which allows gases used during sterilization to enter and exit the pouch but does not allow environmental contaminants in. Pouch 502 may be a self seal or heat seal pouch. Representatively, pouch 502 is a heat seal or self seal Tyvek® pouch available from Tolas Healthcare Packaging, Feasterville, Pa. The container remains in pouch 502 throughout the remainder of the sterilization process and packaging of the container so that the container and contents therein are not exposed to contaminants.

The powder of biodegradable carriers within the container, and in some embodiments the pouch, is then sterilized (block 106). In one embodiment, the biodegradable carriers and the container are sterilized using chemical sterilization techniques. Representatively, the biodegradable carriers and container are sterilized using ethylene oxide gas, gas plasma or a Noxilizer™ technique.

Ethylene oxide (EtO) sterilization is performed by exposing the container with carriers therein to gaseous ethylene oxide according to parameters which obtain a desirable bioburden level. The process is carried out at 30 to 60 degrees C. First humidity is injected into the chamber containing the gas permeable container (dwell time 10-120 minutes). After that ethylene oxide gas is injected into the chamber (dwell time 1-6 hours). Finally the chamber is purged using alternating cycles of vacuum and an inert gas such as argon or nitrogen. Ideally a low temperature (e.g., 30-35 degrees C.) is maintained and dwell times (e.g., 10-30 minutes for vapor, 1-4 hours for EtO) are kept short while still yielding a sterile sample.

The Noxilizer™ technique refers to a room temperature technique in which oxides of nitrogen ($NO_x$: nitric oxide, nitrous oxide, nitrogen dioxide, etc.) are used to sterilize the container with carriers therein. Similar to the previously discussed technique, humidity (e.g., about 40-90 relative humidity) is introduced into the chamber, followed by the $NO_x$ mixture. This process is carried out at room temperature (e.g., about 10-30 degrees C.) for about 10 to 60 minutes. This method allows for the use of lower temperatures with minimal relative humidity compared to EtO Gas plasma sterilization refers to a technique in which gas plasma, for example argon gas plasma, is used to sterilize the container with carriers therein. Gas plasma sterilization may be carried out according to any conditions suitable for sterilizing the containers and carriers without degrading the carriers, containers or treatment agents therein.

Although specific parameters are disclosed for some of the above-described techniques, it is contemplated that any parameters capable of sterilizing the desired materials without degrading the carriers or treatment agents therein may be used.

In another embodiment, sterilization of the container with treatment agent loaded carriers is achieved by radiation sterilization techniques. Radiation sterilization refers to the use of various kinds of radiation, including, but not limited to, electron beam (e-beam), gamma ray, ultraviolet, infra-red, ion beam, x-ray and laser sterilization. A sterilization dose can be determined by selecting a dose that provides a required SAL without modifying the properties or morphology of the carrier.

In this aspect, a known quantity of treatment agent loaded carriers is determined by dispersing the carriers in an aqueous medium or weighing the carriers as previously discussed. Aliquots of the known amount of the carrier with the treatment agent disposed therein are then transferred into containers, such as syringes or vials. The containers are left open and placed in a lyophilizer and lyophilized as previously discussed. The container with treatment agent loaded carriers therein is conditioned as needed to remove any trace amounts of moisture not removed by the lyophilization process and oxygen. Conditioning is performed using a conditioning chamber or a syringe stoppering device with an inert overlay. In this aspect, the atmosphere in the vial, syringe or container is replaced with an inert and dry gas such as argon or nitrogen. First vacuum is applied to the chamber, then the inert gas is introduced. After a given time the container is sealed.

The containers are then sealed by any suitable technique for sterilization. Since radiation passes through the container, the container may be completely sealed to prevent exchange of gases with the atmosphere.

The container and carriers are exposed to a dose of radiation in one or multiple passes. Irradiation refers to the exposure to radiation. Representatively, the containers are placed in a tray or other holder for positioning before the radiation source, for example, an e-beam or gamma ray. E-beam irradiation involves the exposure to concentrated highly charged electrons generated by the acceleration and conversion of electricity. E-beam exposure is performed at room temperature or a controlled, low temperature. Gamma irradiation can penetrate materials of various densities and thus can be used for products in complex packages. Cobalt 60 can be used as a source of gamma rays.

In some embodiments, the container with carriers therein may be sealed within pouches as previously discussed and exposed to a low dose of gamma or e-beam radiation to terminally sterilize the product. Representatively, the low dose of e-beam or gamma rays may be from about 10 kilo gray (kGy) to about 30 kGy. For example, the dose may be from 12 kGy to 25 kGy or from 15 kGy to 20 kGy. Since each component is presumably low bioburden, the radiation dose can be kept low. In addition, it is desirable that the radiation doses keep the molecular weight of the carriers within a desired range to preserve a desired performance of the product. Representatively, the desired molecular weight range of the carriers may be between 50 kDa and 200 kDa. The total dose of, for example, 10 kGy to 30 kGy is delivered in a single pass. A dose of, for example, 15 kGy to 20 kGy allows for a sterile product while minimizing the decrease in molecular weight of the polymer and drug degradation.

To minimize heat effect, the product can be cooled down prior to sterilization, such that the temperature in the product does not exceed the glass transition temperature ($T_g$) of the polymer. In general cooling of the product between −4 and 10 degrees C. is sufficient. The glass transition temperature refers to the temperature at which the amorphous domains of a polymer change from a brittle vitreous state to a solid deformable state. In other words, the $T_g$ corresponds to the temperature where the onset of segmental motion in the chains of the polymer occurs. When an amorphous or semi crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom from the molecules to move. The increasing heat capacity corresponds to an increase in heat dissipation through movement. The measured $T_g$ of a given polymer can be dependent on the heating rate and can be influenced by the thermal history, and potentially pressure history, of the polymer, as well as potentially the pressure at which the measurement is made. Furthermore, the chemical structure of the polymer heavily influences the glass transition by affecting mobility.

In some embodiments, prior to sterilization, an antioxidant (e.g. Butylated hydroxytoluene (BHT)) may be added to the container with carriers therein to protect against moisture or oxidative agents that can affect product shelf life.

To deliver the sterile treatment agent loaded carriers from the container to the desired treatment site, the carriers are re-suspended into a solution (block 108). Representatively, the carriers are re-suspended by adding an amount of sterile saline to the container. In still further embodiments, a viscosity modulating component is added to the solution. The viscosity modulating component includes, but is not limited to, polyethylene oxide, polypropylene oxide, polyvinyl alcohol, contrast media, dextran or glycerine.

Once re-suspended, the solution of treatment agent loaded carriers is loaded into a delivery device and delivered to a treatment site, for example, within a renal system (block 110).

Aseptic Processing

In still further embodiments, an aseptic processing technique is used to sterilize the components (e.g. delivery device, carriers, treatment agent and container) associated with delivery of a treatment agent to the kidney. In this aspect, the delivery device, container and any other associated packaging components (e.g. pouches) are sterilized using EtO or one of the other above-discussed radiation techniques.

A desired amount of the treatment agent for incorporation into carriers is exposed to a low dose of e-beam or gamma ray. Representatively, the low dose of e-beam or gamma rays may be a dose of from about 10 kGy to about 30 kGy. In some embodiments, exposure may be at a low or cold temperature (e.g., −4 to 10 degrees C.). The desired amount of treatment agent for incorporation into carriers is determined by using sterile water or a solvent and aseptic processing to meter the precise dose of treatment agent.

The carriers are sterilized by exposing a carrier solution (e.g. PLGA dissolved in organic solvent) to a low dose of radiation. In still further embodiments, a solvent or cool gas (e.g., NOx or EtO) may be used to sterilize the carrier solution.

The measured amount of treatment agent is combined with the sterilized carrier solution to form carriers loaded with the treatment agent. Aliquots of the treatment agent loaded carrier solution are placed in containers and then lyophilized or subjected to an aqueous flash-off treatment to remove any liquid. Prior to and/or after removal of any liquid, the container with carriers therein may be sealed within a pouch as previously discussed. The aseptic technique disclosed herein is consistent with regulatory requirements to achieve a SAL of $1\times10^{-6}$.

Treatment Agents

As used herein, treatment agents are intended to include, but are not limited to, drugs, biologically active agents, chemically active agents, therapeutic agents, and the like, and pharmaceutical compositions thereof, which can be used to deliver a treatment agent to a treatment site within a kidney as described herein. The treatment agents are delivered alone or in combination to the treatment site.

In one embodiment, the treatment agent includes a property to inhibit a biological process contributing to nephropathy. Such biological processes include, but are not limited to, changes in glomerular basement membrane, changes in mesangial matrix deposition and podocyte attachment and/or apoptosis.

In one embodiment, the treatment agent includes a drug. The drug may have a property to inhibit undesirable effects of the renin-angiotensin system in the kidneys. The renin-angiotensin system responds to a decrease in the perfusion of the juxtaglomerular apparatus found in afferent arterioles of the glomerulus of the kidney by constricting glomerular arterioles. Such constriction causes blood to build up in the glomerulus and increase glomerular pressure. Representative drugs that act to inhibit this process include, but are not limited to, angiotensin converting enzyme (ACE) inhibitors, angiotensin receptor blockers (ARBs) and renin inhibitors.

In still further embodiments, the treatment agent includes a drug to inhibit protein kinase C. Representative drugs include, but are not limited to, ruboxistaurin (LY333531), enzastaurin (LY317615), bisindolylmaleimide IX, chelerythrine, edelfosine, edelfosina, ET18OCH3, H-7, HA-100, H89, HA-1004, Ro 31-8220, rottlerin, staurosporine and quercetin.

The transforming growth factor-beta system contributes to the progression of renal damage due to stimulation of extracellular matrix deposition. Thus, in further embodiments, the treatment agent includes an agent having a property to inhibit the synthesis or activity of transforming growth factor beta, its receptor and SMAD and other signaling molecules downstream of the receptor. Representative inhibitors include, but are not limited to antisense molecules, ribozymes, siRNA, antibodies, receptor kinase inhibitors and other small molecule inhibitors such as halofuginone, sirolimus, everolimus, biolimus ABT578 and nuclear receptor agonists such as estradiol, retinoids, and peroxisome proliferator-activated receptors (PPAR) agonists.

It is further recognized that connective tissue growth factor (CTGF) is present in glomeruli in patients with diabetic nephropathy. CTGF is a member of the centrosomin (CCN) family of proteins, which regulate biological processes including stimulation of cell proliferation, migration, and adhesion. It is believed that expression of CTGF in diabetic kidneys contributes to the development of glomerulosclerosis by affecting matrix synthesis and its turnover. In this aspect, the treatment agent includes an agent having a property to inhibit the synthesis of or activity of connective tissue growth factor. Representative agents having a property to inhibit connective tissue growth factor include, but are not limited to, antibodies, interleukin-1 (IL-1) alpha and beta, Rho A GTPase inhibitors, and p38 MAP kinase inhibitors.

In some embodiments, the treatment agent is an immunosuppressant such as zotarolimus.

In some embodiments, the treatment agent is modified to enhance uptake of the agent into the desired tissue. In this aspect, the treatment agent is delivered to the desired tissue in a formulation which includes vasoactive agents as enhancers of vascular permeability called excipients, such as thrombin, bradykinin and histamine. These excipients have properties which increase endothelial porosity and thereby enhance uptake of the treatment agent into the tissue.

As previously discussed, the treatment agent is delivered in a form including, but not limited to, a solution. For example, in some embodiments, a desired amount of treatment agent is mixed with saline or an iodine free-contrast media to form the solution.

Carriers

In some embodiments, the treatment agent is delivered to the desired tissue in a carrier. A "carrier" includes a matrix that contains one or more treatment agents. A suitable carrier may take the form of a nanoparticle (e.g., nanosphere) or microparticle (e.g., microsphere). The carrier with the treatment agent encapsulated inside is incorporated into a solution for delivery to the desired tissue.

The carrier is a biodegradable carrier infused with a treatment agent. As previously discussed, the carrier is made of an encapsulation polymer such as poly(lactic-co-glycolic acid) (PLGA). It is further contemplated that other suitable materials for the carrier can include, but are not limited to, polymers such as poly (L-lactide), poly (D,L-lactide), poly (glycolide), poly (lactide-co-glycolide), polycaprolactone, polyanhydride, polydiaxanone, polyorthoester, polyamino acids, or poly (trimethylene carbonate), and combinations thereof. Suitable materials for the carrier may further include copolymers such as, but not limited to, polyethylene oxide and poly propylene oxide.

Carriers having a size greater than about 10 microns have the potential, when introduced into the renal artery, of being trapped in the glomerular capillaries. In this aspect, the treatment agent is released over time at a point within the glomerular capillaries. In other embodiments, the carrier size is between about 1 micron to 100 microns, still further between about 8 microns to about 15 microns and in some embodiments between about 1 micron to 2 microns. In other embodiments, the carrier size is between about 10 microns and 14 microns. In still further embodiments where the treatment agent is delivered at a point outside of a vessel lumen, such as the kidney cortex, the treatment agent or a carrier encapsulating the treatment agent is any size capable of being delivered through a lumen of the delivery device, such as for example, a size as small as one nanometer (nm) to as large as about 100 microns.

In some embodiments, the carrier is a sustained-release carrier which allows for controlled release of the treatment agent over time at the desired treatment site. Representatively, the carrier degrades within the body and release the treatment agent over a period of five to six months. Examples of sustained-release polymers used to form the carriers include, but are not limited to, PLGA, PLA or PLA-PEEP co-polymers, poly-ester-amide co-polymers (PEA) and PLA-PEG.

Various methods are employed to formulate and infuse the carrier with one or more treatment agents. The embodiments of the composition of infused carrier are prepared by conventional methods where all components are combined then blended. In some embodiments, carriers are prepared using a predetermined amount of a polymer or a pre-polymer that is added to a predetermined amount of a solvent or a combination of solvents. The solvent is mutually compatible with the polymer and is capable of placing the polymer into solution at the concentration desired in the solution. Examples of solvents include, but are not limited to, dimethylsulfoxide (DMSO), Dimethyl Acetamide (DMAC), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methylpyrrolidinone, toluene and mixtures thereof.

By way of example, and not limitation, the polymer comprises from about 50% or more by weight of the total weight of the total solution, and the solvent comprises from about 65% to about 99.9%, more narrowly about 80% to about 98% by weight, of the total weight of the total solution. A specific weight ratio is dependent on factors such as the material from which the delivery device is made and the geometrical structure of the device.

Sufficient amounts of treatment agent are dispersed or dissolved in the carrier. The amount of treatment agent introduced into the carrier is any amount sufficient to inhibit a biological process contributing to nephropathy when released within the renal system. The treatment agent is in solution or suspension. If the treatment agent is not completely soluble in the composition, operations including mixing, stirring, and/or agitation is employed to effect homogeneity. The treatment agent is added so that the dispersion is in fine particles. The mixing of the treatment agent is conducted in an anhydrous atmosphere, at ambient pressure and at room temperature.

In some embodiments using microparticles (e.g. microspheres) and/or nanoparticles (e.g. nanospheres), the microparticles and/or nanoparticles are sustained release carriers prepared by a water/oil/water (W/O/W) double emulsion method. The W1 phase, an aqueous phase containing treatment agent, is dispersed into the oil phase consisting of polymer (e.g. PLGA) dissolved in organic solvent (e.g., dichloromethane) using a high-speed homogenizer. The primary water-in-oil (W/O) emulsion is then dispersed to an aqueous solution containing a polymeric surfactant, e.g., poly(vinyl alcohol) (PVA), and further homogenized to produce a W/O/W emulsion. After stirring for several hours, the microparticles and/or nanoparticles are collected by filtration.

In some embodiments, a surface of the carrier is modified to enhance affinity of the encapsulated treatment agent to tissue lining the walls of the glomerular capillaries. In this aspect, the surface is coated with binding agents. The binding agent may include a protein or small molecule that will facilitate retention of the carrier and encapsulated treatment agent at the treatment site so as to induce and/or modulate a therapeutic response through interaction with a specific binding site (e.g., a receptor within a cell or on a cell surface). Representative binding agents and their associated receptors include, but are not limited to, CD11/CD18 (MAC-1) or aL/beta2 integrin (LFA-1) and intracellular adhesion molecule-1 (ICAM-1) receptor, integrin avb3 which binds to RGD-containing peptide and E-selectin which binds to Sialyl-Lewis glycoprotein.

In some embodiments, a surface charge of the carrier is further modified (e.g. positively, negatively or neutral) to accommodate and enhance binding characteristics to the glomerular tissue. The endothelial cells and basement membrane along the normal glomerular capillary walls are typically electronegatively charged. As diseases such as glomerulosclerosis and diabetic nephropathy progresses, however, these cells slowly lose the electronegative charge. It is believed that modifying the carriers to have an electropositive charge will enhance binding of the carrier and encapsulated agent within the capillary. In this aspect, a carrier encapsulating the treatment agent is modified by any standard method suitable for providing the carrier surface with an electropositive charge. In one embodiment, positively charged carriers are made by coating carriers with Chitosan. Alternatively, positively charged carriers are made, for example, entirely of Chitosan in a water-in-oil emulsion process and crosslinked with glutaraldehye or genipin. In this aspect, the treatment agent is swell loaded in the crosslinked spheres. Still further, if the treatment agent is soluble at pH 5, the treatment agent is incorporated into the initial Chitosan solution, provided it does not subsequently react with the aldehyde crosslinker. Another approach for forming cationic carriers includes using a poly-lysine graft of PLGA.

In still further embodiments, a surface of the carrier is coated with active agents or other species to enhance the range of functionalities of the product. For example, the surface is coated with a monoclonal antibody that selectively binds to proteins expressed within the glomerulus (glomerular endothelium, basement membrane, podocytes) and tubules (tubular epithelium and basement membrane). A representative example is the monoclonal antibody anti CD90/Thy 1 that binds to OX-7 a glomerular basement membrane protein. Other proteins to target include nephrin and podocin.

In some embodiments the container having the sterile powder of carriers therein is packaged in the form of a kit. The kit includes at least one container having a predetermined quantity of the powder of sterilized biodegradable carriers with the treatment agent disposed therein. Representatively, the container may be a syringe or vial. The container may hold a quantity of carriers having an amount of treatment agent therein suitable for treating a single treatment region (e.g. a kidney). The kit further includes a delivery device for delivering the predetermined quantity of sterilized biodegradable carriers with the treatment agent disposed therein to the treatment site. In some embodiments, the kit includes an amount of a liquid suitable for re-suspending the powder of sterilized biodegradable carriers with the treatment agent disposed therein. Representatively, the liquid is saline. The kit may also include a viscosity modulator to modify a viscosity of a solution comprising the powder of sterilized biodegradable carriers with the treatment agent disposed therein.

Figure 2:
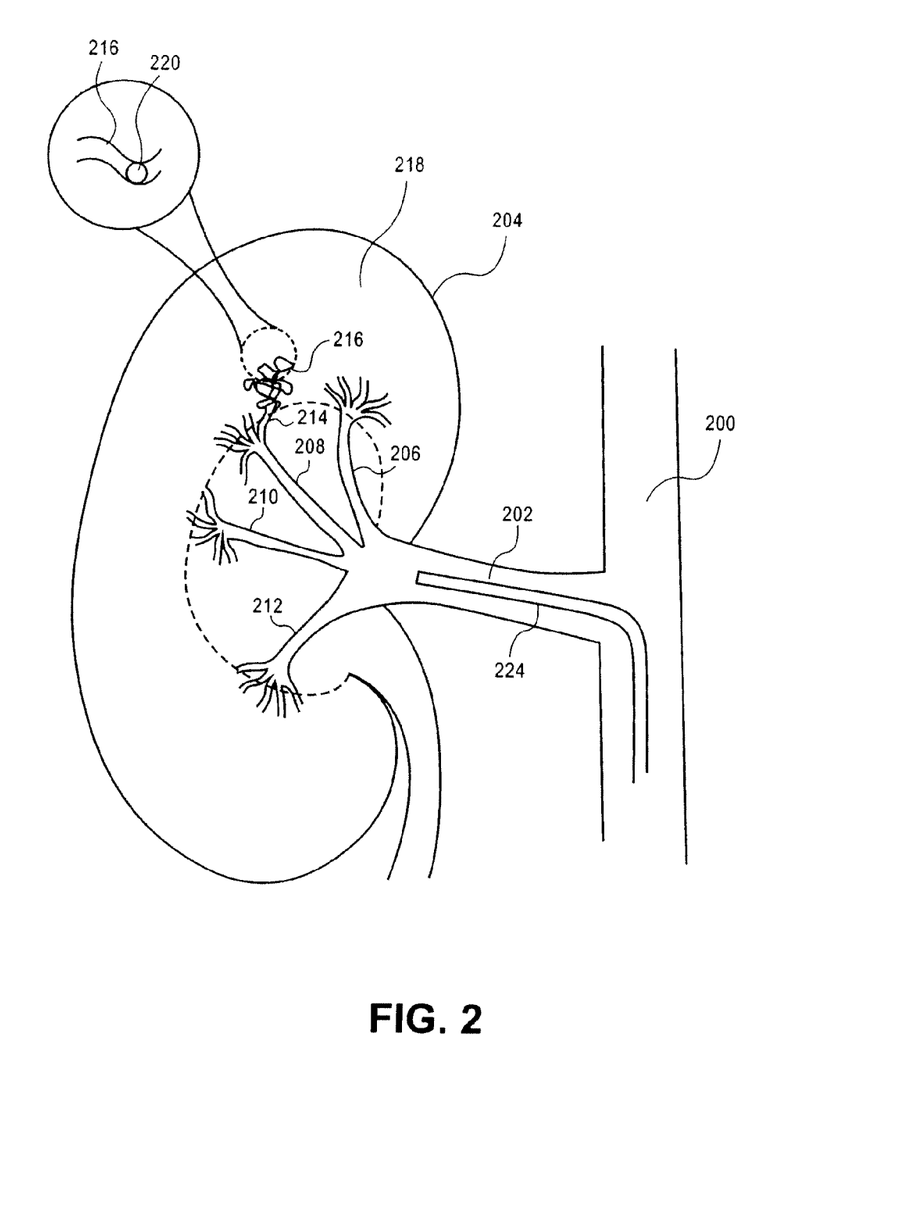
FIG. 2 shows a cross-sectional side view of a kidney and a method for delivering a treatment agent to the kidney.

FIG. 2 shows a cross-sectional side view of a kidney and a method for delivering a treatment agent to the kidney. As illustrated in FIG. 2, a lower branch of aorta 200 feeds blood to kidney 204 through renal artery 202. Renal artery 202 branches off into renal segmental arteries 206, 208, 210 and 212 and arterioles 214. Each arteriole 214 in turn leads to a tuft of capillaries 216, also known as a glomerulus. Blood from segmental arteries 206, 208, 210 and 212 flows into the glomerulus at the end of each segmental artery 206, 208, 210 and 212 where it is filtered to remove fluid and solutes from the blood. In one embodiment, as illustrated in FIG. 2, a distal end of delivery device 224 is positioned at a point within renal artery 202. Alternatively, delivery device 224 is positioned at a point within renal segmental arteries 206, 208, 210 and 212. A proximal portion of delivery device 224 remains outside of the body to facilitate loading of the treatment agent within delivery device 224. Representatively, a femoral artery is punctured and delivery device 224 is advanced through the femoral artery, to aorta 200 and then into renal artery 202. Alternatively, delivery device 224 is advanced through a brachial artery, down aorta 200 and into renal artery 202. In still further embodiments, an external iliac artery is punctured and delivery device 224 is advanced through the external iliac artery to a common iliac artery, to aorta 200 and then into renal artery 202.

It is further contemplated that delivery device 224 is introduced to a point within kidney 204 via a retroperitoneal insertion technique. In this aspect, a distal end of delivery device 224 is inserted through a back of a patient adjacent kidney 204. Delivery device 224 is then advanced through a surface of kidney 204 to a point within renal cortex 218 adjacent to glomerulus 216. In this aspect, when the treatment agent is delivered via delivery device 224, the treatment agent is localized to an area proximal to glomerular capillaries within the kidney to facilitate treatment of the kidney. Alternatively, delivery device 224 is introduced through a back region of the patient and into renal artery 202. In this embodiment, the treatment agent is then delivered by delivery device 224 through renal artery 202 to a desired treatment site.

In an embodiment illustrated in FIG. 2, a treatment agent loaded carrier within delivery device 224 is released into, for example, renal artery 202 such that the treatment agent flows through segmental artery 208 and into glomerulus 216. In one embodiment, the carrier has a large enough diameter such that the carrier becomes lodged within a narrow lumen of a capillary within the glomerulus 216. This aspect is shown in the exploded view of glomerulus 216 of FIG. 2. In this embodiment, treatment agent 220 flows into glomerulus 216 and becomes lodged within the lumen. For example, in some embodiments the treatment agent is loaded into, for example, a microsphere having a diameter from about 8 microns to about 15 microns. Release of the treatment agent from within the carrier is localized to glomerulus 216. Thus, delivery of the treatment agent is confined to a specific treatment site within the kidney.

Delivery Devices

The term delivery device is intended to broadly include any medical device for insertion into a physiological lumen to permit injection and/or withdrawal of fluids of varying viscosities to maintain patency of a lumen of a blood vessel or an area defining the lumen, or for other purposes. The delivery device may further include any medical device for insertion into a physiological lumen capable of releasing a treatment agent. The point to which the delivery device is introduced is a treatment site or a region adjacent to a treatment site. The treatment site is a diseased region within a renal vessel or other tissue of a kidney.

Typically, the flow profile of blood flowing through the renal artery to the kidney is laminar, meaning the fluid flows in parallel layers, or streams, with little or no disruption between the layers. This profile continues along the kidney opening, or hilum, and into the segmental arteries leading to the glomerular capillaries within the renal cortex. Thus, when the treatment agent is released from a single point of a delivery device into one of these streams of a healthy kidney most, if not all, of the treatment agent is carried only to the kidney region at the end of the stream. In this aspect, only a small portion of the kidney receives the treatment agent. Moreover, blood flow to the diseased regions especially in need of the treatment agent is reduced or stop all together as a result of the disease. In such cases, even where the treatment agent is released into a path normally destined for the diseased region, it will not reach the desired treatment region. Thus, it is desirable to deliver the treatment agent solution to the kidney using devices which overcome these issues (e.g. create a turbulent blood flow within the vessel by, for example, partially occluding a region of the artery lumen so as to provide a constricted pathway for blood flow (e.g., about 60% to about 95% lumen occlusion)).

It is further contemplated that the delivery device is one which prevents backflow of the treatment agent. The term "backflow" as used herein generally refers to a flow of treatment agent in a direction opposite to that in which it is desired to be delivered.

Figure 3:
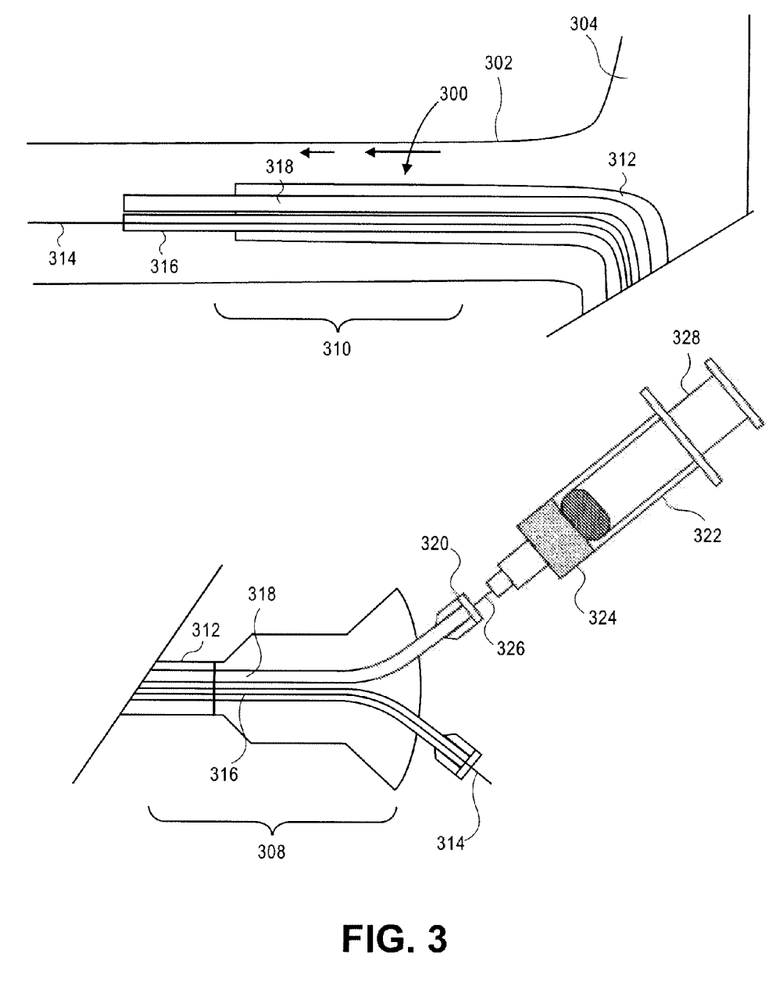
FIG. 3 shows a cross-sectional side view of a blood vessel of a renal region and an embodiment of a delivery system to deliver a treatment agent to a kidney.

FIG. 3 shows blood vessels of a renal region and one embodiment of a delivery system to deliver a treatment agent to a kidney. FIG. 3 shows a renal artery 302 extending from aorta 304 and having a delivery device 300 disposed therein. Delivery device 300 includes a proximal portion 308 and a distal portion 310. Proximal portion 308 is external to renal artery 302 and to the patient. Representatively, delivery device 300 is inserted through a femoral artery and through, for example, a guide catheter and with the aid of a guidewire 314 to a location in a renal artery or renal segmental artery of a patient. Alternatively, delivery device 300 is introduced to the point within the renal system of the patient by inserting delivery device 300 through a region of the patient's back adjacent a kidney and then advancing delivery device 300 into the kidney renal cortex or a renal artery. FIG. 3 shows distal portion 310 of delivery device 300 positioned at a point within renal artery 302. Alternatively, delivery device 300 is positioned at a point within a renal segmental artery or a renal cortex.

In one embodiment, delivery device 300 includes a primary cannula 312 having a length that extends from proximal portion 308 (e.g. located external to a patient during a procedure) to distal portion 310. Primary cannula 312 has a lumen therethrough sized to accommodate guidewire cannula 316 and delivery cannula 318. It is contemplated that primary cannula 312 is a single lumen catheter as illustrated in FIG. 3 or, in some embodiments, a dual lumen catheter. In some embodiments where delivery device 300 is introduced to a location within a renal artery, guidewire cannula 316 and delivery cannula 318 have a width of about 5 French to about 7 French (3 French=1 mm). In other embodiments where delivery device 300 is introduced to a location within a renal segmental artery, guidewire cannula 316 and delivery cannula 318 have a width of about 2 French to about 4 French.

Delivery cannula 318 extends from proximal portion 308 of delivery device 300 to distal portion 310. Delivery cannula 318 has a distal end that is open to allow for delivery of a treatment agent within renal artery 302. In one embodiment, the treatment agent is loaded within biodegradable carriers and delivered from container 322 as previously discussed. In some embodiments, container 322 is a syringe. To deliver the sterilized biodegradable carriers with the treatment agent disposed therein from syringe 322, the biodegradable carriers are re-suspended by drawing a liquid (e.g. saline) into syringe 322 through needle 326. In some embodiments, a filter (e.g. 0.2 micrometer filter) is positioned between needle 326 and the body of syringe 322 to maintain sterility of the re-suspending liquid. Needle 326 of syringe 322 is positioned within delivery port 320 of delivery cannula 318. Plunger 328 is depressed to eject the solution of biodegradable carriers 324 from syringe 322 and into delivery cannula 318. The solution of biodegradable carriers 324 travels through delivery cannula 318 and out the open distal end to renal artery 302.

Alternatively, delivery cannula 318 has an occluded distal end and holes disposed along a length of the distal end extending beyond primary cannula 312 so that the treatment agent is emitted from the holes in a direction perpendicular to the direction of blood flow. Delivery of the treatment agent perpendicular to the direction of blood flow, in addition to the narrowing of the vessel lumen due to device 300, disrupts the blood flow thereby creating turbulent conditions. The turbulence facilitates mixing of the treatment agent into the blood flow and even distribution of the treatment agent at the desired treatment site, for example, distal to delivery device 300. Additionally, emitting the treatment agent out of the sides of the device in this manner does not increase a flow rate of fluid (e.g. mixture of blood and treatment agent) delivered to the treatment site therefore backflow from the delivery of the mixture of blood and treatment agent into the treatment site is minimized.

Guidewire cannula 316 has a lumen sized to accommodate a guidewire 314. Delivery device 300 is an over the wire (OTW) configuration wherein guidewire cannula 316 extends from a proximal end (e.g., external to a patient during a procedure) to a distal end of delivery device 300. Guidewire cannula 316 can also be used for delivery of a treatment agent such as an agent having a property to inhibit nephropathy or a formulation including vasoactive agents which enhance binding characteristics to glomeruli of the kidney when guidewire 314 is removed with delivery device 300 in place. In such case, separate delivery cannula (i.e., delivery cannula 318) is unnecessary. Alternatively, delivery cannula 318 is used to deliver one treatment agent while guidewire cannula 316 is used to deliver another treatment agent.

In another embodiment, catheter assembly 300 is a rapid-exchange-type (RX-type) delivery device and only a portion of catheter assembly 300 (e.g., a distal portion 310) is advanced over guidewire 314. In a RX-type of delivery device, typically, the guidewire cannula extends from the distal end of the delivery device to the proximal guidewire port which is typically spaced a substantial distance from the proximal end of the delivery device.

Figure 4:
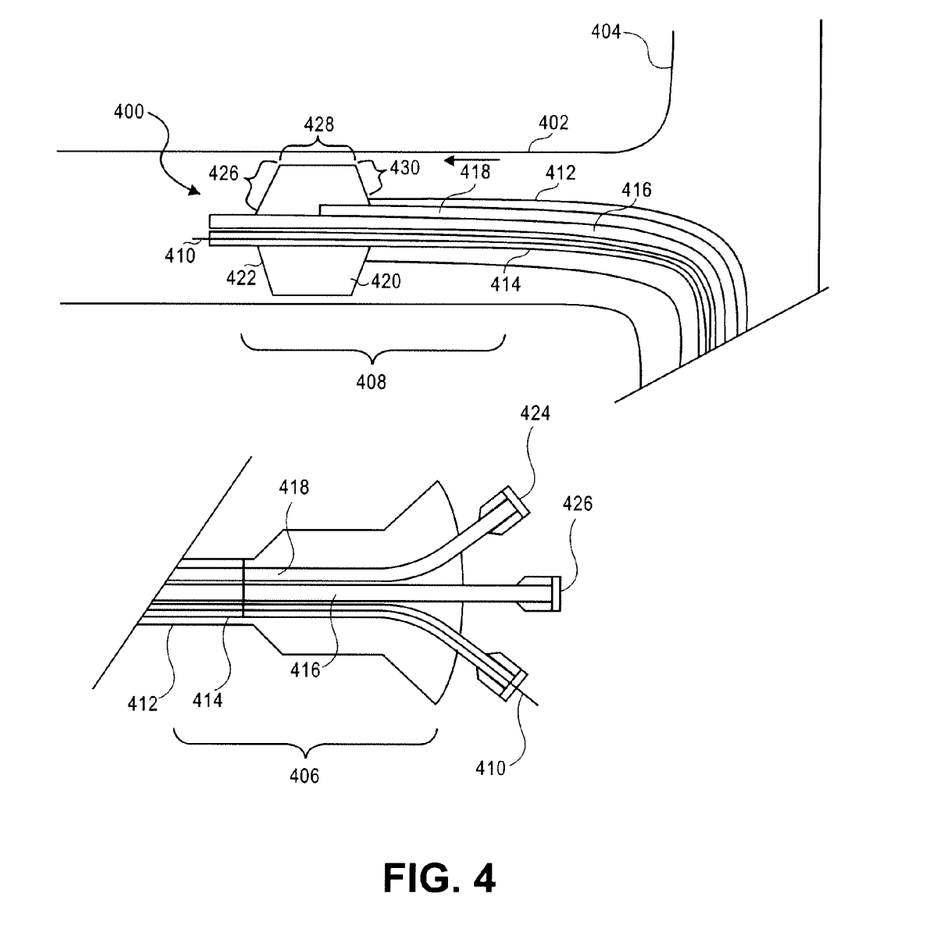
FIG. 4 shows a cross-sectional side view of a blood vessel of a renal region and an embodiment of a delivery system to deliver a treatment agent to a kidney.

FIG. 4 shows a blood vessel of a renal region and another embodiment of a delivery system to deliver a treatment agent to a kidney. FIG. 4 shows a renal artery 402 branching off of aorta 404 and having a delivery device 400 disposed therein. Delivery device 400 includes a proximal portion 406 and a distal portion 408. Proximal portion 406 is external to renal artery 402 and to the patient. Representatively, delivery device 400 is inserted through a femoral artery and through, for example, a guide catheter and with the aid of a guidewire 410 to a location in a renal artery or renal segmental artery of a patient. FIG. 4 shows distal portion 408 of delivery device 400 positioned at a point within renal artery 402. Alternatively, delivery device 400 is positioned at a point within a renal segmental artery.

In one embodiment, delivery device 400 includes a primary cannula 412 having a length that extends from proximal portion 406 (e.g. located external to a patient during a procedure) to connect with a proximal end or skirt of balloon 420. Primary cannula 412 has a lumen therethrough that includes guidewire cannula 414, delivery cannula 416 and inflation cannula 418. Delivery cannula 416 extends from proximal portion 406 of delivery device 400 to distal portion 408. Inflation cannula 418 further extends from proximal portion 406 of delivery device 400 to distal portion 408. Inflation cannula 418 has a distal end that terminates within balloon 420. In one embodiment, catheter assembly 400 is introduced into renal artery 402 and balloon 420 is inflated via inflation cannula 418.

Primary cannula 412, as well as those described in reference to other embodiments, is a polymer material that may include markers to allow the cannula to be identified using fluoroscopic or angiographic techniques. For example, a metal band (e.g., stainless steel, platinum, or tungsten loaded polymer) that is detected by fluoroscopic or angiographic techniques.

Balloon 420 is connected to a distal end of delivery device 400 and is in fluid communication with inflation cannula 418. Balloon 420 includes balloon wall or membrane 422 which is selectively inflatable to dilate from a collapsed configuration to a desired and controlled expanded configuration. Balloon 420 can be selectively expanded by supplying a fluid into inflation cannula 418 at a predetermined rate of pressure through delivery port 424. Balloon wall 422 is selectively deflatable, after inflation, to return to the collapsed configuration or a deflated profile. In one embodiment, balloon wall 422 is defined by three sections, distal taper wall 426, medial working length 428, and proximal taper wall 430. In one embodiment, proximal taper wall 430 tapers at any suitable angle θ, typically between about 10° to less than about 90°, when balloon 420 is in the expanded configuration.

Distal taper wall 426, medial working length 428, and proximal taper wall 430 of balloon wall 422 are bound together by seams or be blown out of a single seamless material. Balloon 420 is made from any suitable material, including, but not limited to, polymers and copolymers of polyolefins, polyamides, polyesters and the like. The specific material employed must be mutually compatible with the fluids employed in conjunction with balloon 420 and must be able to withstand the pressures that are developed within balloon 420. Balloon wall 422 can have any suitable thickness so long as the thickness does not compromise properties that are critical for achieving optimum performance. Such properties include high burst strength, low compliance, good flexibility, high resistance to fatigue, the ability to fold, the ability to cross and re-cross a desired region of treatment or an occluded region in a lumen, and low susceptibility to defect caused by handling. By way of example, and not limitation, the thickness can be in the range of about 0.0005 inch to about 0.003 inch, the diameter of balloon 320 in the expanded configuration can be in the range of about 2 millimeters (mm) to about 10 mm, and the length can be in the range of about 3 mm to about 40 mm. The specific specifications, however, may vary depending on the procedure for which balloon 420 is to be used and the anatomy and size of the target lumen in which balloon 420 is to be inserted.

Balloon 420 is expanded by the introduction of a liquid into inflation cannula 418. In one embodiment where balloon 420 has micropores, liquids containing therapeutic and/or diagnostic agents are delivered through inflation cannula to inflate balloon 420. In this aspect, delivery cannula 416 may be omitted. In other embodiments, delivery cannula 416 has a distal end terminating in balloon 420 and inflation cannula 418 is removed. In this aspect, a treatment agent such as those described above is introduced through a delivery lumen (e.g., inflation cannula 418) to expand the balloon (e.g., balloon 420). The treatment agent will expand balloon 420 at relatively low pressure (e.g., 2-3 atm) and diffuse through the pores to a treatment site, such as glomerular capillaries, within the kidney. In some embodiments, the balloon is expanded to a dimension which partially occludes artery 402 such that blood continues to flow past balloon 420. Partial occlusion provides a turbulent blood flow distal to delivery device 400 due to the narrowing of the region through which the blood must pass. Partial occlusion includes from about 60% to about 95% lumen occlusion. In this aspect, the treatment agent is infused into the turbulent blood flow through the pores or an end of delivery cannula 416 distal to balloon 420 into a turbulent blood flow distal to delivery device 400. In this aspect, a homogenous distribution of the treatment agent within the blood flowing to the kidney is achieved. Still further, since the balloon is inflated, backflow is minimized.

In another embodiment, delivery device 400 includes a perfusion shaft (not shown) to allow blood to continue to flow to a vessel region distal to balloon 420 when balloon 420 is fully inflated to occlude the vessel lumen. In this embodiment, primary cannula 412 is omitted and guidewire cannula 414 includes holes through portions of a wall of guidewire cannula 414 located proximal and distal to balloon 420. In this aspect, guidewire 410 is positioned proximal to an end of guidewire cannula 414 (e.g., about 10 centimeters from the end), and more specifically proximal to the openings, such that blood is free to flow into holes proximal to balloon 420, through guidewire cannula 414 and out the holes of guidewire cannula 414 distal to balloon 420. In this aspect, although the vessel lumen is completely occluded, blood continues to flow to a region upstream from balloon 420 and a turbulent blood flow is created within this region. Alternatively, balloon 420 is nonporous and delivery cannula 416 is used to deliver a treatment agent to a region downstream from balloon 420.

The treatment agent is delivered to the desired treatment site through delivery cannula 416 or inflation cannula 418 from a sterilized container (e.g. a syringe) having a predetermined amount of the treatment agent disposed within biodegradable carriers as discussed in reference to FIG. 3. In this aspect, where the container is a syringe, a needle of the syringe is positioned within delivery cannula port 426 or inflation cannula port 424 and the syringe plunger depressed to expel the treatment agent solution out of the syringe and into delivery cannula 416 or inflation cannula 418.

Although a substantially round balloon is shown in FIG. 4, it is contemplated that for this embodiment, balloon 420 may have any shape deemed desirable for occluding the lumen of blood vessel 402, for example, conical/square, tapered stepped, and offset.

In one embodiment, balloon 420 is a conventional nonporous balloon. In other embodiments, balloon 420 is a porous material such as PEBAX®, Nylon or polyethylene terephthalate (PET) that has tens or hundreds of micropores around its circumference for treatment agent diffusion. A suitable pore size may range, for example, from about 4 microns to about 400 microns, in some embodiments from about 10 microns to about 100 and in some embodiments from about 8 microns to about 15 microns. Still further, the pore size may have a size of at least four times the diameter of a particle to be delivered. Pores are created by mechanical means or by laser perforation. Pore distribution along a balloon surface is inhomogeneous to tailor distribution of treatment agent delivery. Balloon 420 is also retractable into optional sheath (not shown) to tailor a length of a treatment agent delivery region. In an alternative embodiment, the sheath has an opening on one side to preferentially deliver a treatment agent to one side of the vessel.

Guidewire cannula 414 extends through balloon 420. Guidewire cannula 414 has a lumen sized to accommodate a guidewire 410. Delivery device 400 is an over the wire (OTW) configuration wherein guidewire cannula 414 extends from a proximal end (external to a patient during a procedure) to a distal end of delivery device 400. Guidewire cannula 414 is also used for delivery of a treatment agent as previously described such as an agent having a property to inhibit nephropathy or a formulation including vasoactive agents which enhance binding characteristics to glomerular tissue of the kidney when guidewire 410 is removed with delivery device 400 in place. In such case, separate delivery cannula (i.e., delivery cannula 416) is unnecessary or a delivery cannula is used to deliver one treatment agent while guidewire cannula 414 is used to deliver another treatment agent.

In another embodiment, delivery device 400 is a RX-type catheter assembly and only a portion of delivery device 400 (e.g., a distal portion 408 including balloon 420) is advanced over guidewire 410. In a RX-type of catheter assembly, typically, the guidewire cannula/lumen extends from the proximal end of the catheter assembly. The proximal guidewire port is typically spaced a substantial distance from the proximal end of the catheter assembly.

Figure 5:
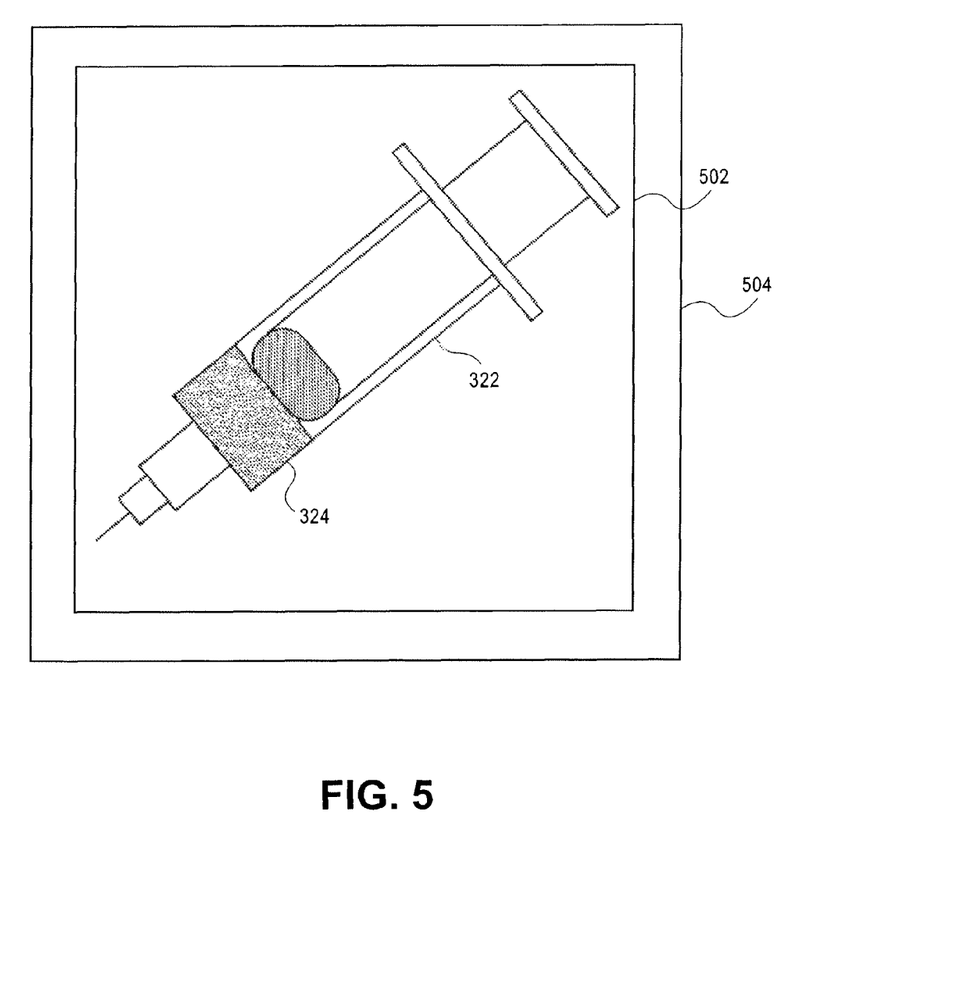
FIG. 5 shows a cross-sectional side view of a packaged sterilized container with carriers.

FIG. 5 shows a cross-sectional side view of a packaged sterilized container with carriers. Container 322 includes a solution of sterilized treatment agent loaded carriers 324 therein. As previously discussed, container 322 is sealed within porous pouch 502 and then sterilized. Pouch 502 having sterilized container 322 and carrier solution 324 is then sealed within an outer pouch 504. Outer pouch 504 can be a pouch made of a material which prevents sterilized container 322 and carrier solution 324 from being exposed to air and humidity. Representatively, outer pouch 504 is an aluminum lined pouch. In some embodiments, an inert gas overlay is provided within outer pouch 504 to further protect container 322 and carrier solution 324 within pouch 502 from contaminants. Representatively, the inert gas is argon or nitrogen. In still further embodiments, dessicants are provided within outer pouch 504 to remove any residual moisture. Suitable dessicants include, but are not limited to, calcium oxide and silica gel.

In the preceding detailed description, specific embodiments are illustrated, including a variety of methods for packaging accurate amounts of sterilized treatment agent loaded carriers and delivering the treatment agent to a kidney region. It will, however, be evident that various modifications and changes are made thereto without departing from the broader spirit and scope of the invention as set forth in the claims. For example, the treatment agent loaded into the carrier can be one used for treatment of tissue regions other than those found within the kidney. It is therefore contemplated that the methods and kit disclosed herein are suitable for delivering a treatment agent to a treatment site within any blood vessel or organ of the body. The specification and drawings are, accordingly, to be regarded in an illustrative rather than a restrictive sense.

What is claimed is:

1. A method comprising:
   introducing a predetermined quantity of biodegradable carriers having a treatment agent disposed therein into a container, wherein the biodegradable carriers comprise nanoparticles or microparticles and are introduced into the container in the form of a solution;
   lyophilizing the predetermined quantity of biodegradable carriers to form a powder within the container, wherein lyophilizing comprises exposing the biodegradable carriers to a reduced pressure of less than $10^{-5}$ Mpa;
   after lyophilizing, conditioning the powder of biodegradable carriers to remove moisture, wherein conditioning comprises applying a vacuum to the container followed by introducing an inert gas into the container, wherein the inert gas is one of a nitrogen gas and an argon gas;

after conditioning, cooling the powder of biodegradable carriers; and after cooling, sterilizing the container and the conditioned powder of biodegradable carriers, wherein sterilizing comprises exposing the container and the biodegradable carriers to one of a gamma ray or an electron beam.

2. The method of claim 1 further comprising:

placing the lyophilized biodegradable carriers and container in a porous pouch prior to sterilizing.

3. The method of claim 1 wherein the treatment agent is capable of inhibiting a biological process contributing to nephropathy.

4. The method of claim 1 wherein the container is a syringe.

5. The method of claim 4 further comprising:

placing a filter over a tip of the syringe prior to sterilizing.

6. The method of claim 1 wherein the container with the biodegradable carriers are exposed to one of the gamma ray or the electron beam at a dose of from 10 kGy to 30 kGy.

7. The method of claim 1 further comprising:

sealing the sterilized container with the sterilized biodegradable carriers therein within a pouch impermeable to humidity and air.

8. The method of claim 1 further comprising:

introducing an antioxidant into the container to protect the biodegradable carriers from moisture and oxidative agents.

9. The method of claim 1 wherein conditioning is performed while the powder of biodegradable carriers is within the container.

10. The method of claim 1 wherein the treatment agent is an mTOR inhibitor selected from one of everolimus or zotarolimus.

11. The method of claim 1 wherein the biodegradable carriers are made of a polymer selected from the group consisting of poly(lactic-co-glycolic acid) (PLGA), poly (L-lactide), poly (D,L-lactide), poly (glycolide), poly (lactide-co-glycolide), polycaprolactone, polyanhydride, polydiaxanone, polyorthoester, polyamino acids, and poly (trimethylene carbonate).

12. The method of claim 1 wherein the nanoparticles or microparticles have a size of from 1 micron to 100 microns.

13. The method of claim 1 wherein cooling comprises cooling the powder of biodegradable carriers to a temperature of between −4 degrees Celsius and 10 degrees Celsius.

* * * * *